United States Patent
Bothof et al.

(10) Patent No.: US 9,616,394 B2
(45) Date of Patent: Apr. 11, 2017

(54) GRAFT COPOLYMER FUNCTIONALIZED ARTICLE

(71) Applicant: 3M INNOVATIVE PROPERTIES COMPANY, St. Paul, MN (US)

(72) Inventors: Catherine A. Bothof, Stillwater, MN (US); George W. Griesgraber, Eagan, MN (US); James I. Hembre, Plymouth, MN (US); Jerald K. Rasmussen, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 248 days.

(21) Appl. No.: 14/400,810

(22) PCT Filed: May 23, 2013

(86) PCT No.: PCT/US2013/042330
§ 371 (c)(1),
(2) Date: Nov. 13, 2014

(87) PCT Pub. No.: WO2013/184366
PCT Pub. Date: Dec. 12, 2013

(65) Prior Publication Data
US 2015/0136698 A1    May 21, 2015

Related U.S. Application Data

(60) Provisional application No. 61/655,516, filed on Jun. 5, 2012.

(51) Int. Cl.
| B01D 71/78 | (2006.01) |
| B01D 71/56 | (2006.01) |
| B01D 71/40 | (2006.01) |
| B01D 71/76 | (2006.01) |
| C09D 179/02 | (2006.01) |
| G01N 33/543 | (2006.01) |
| C09D 177/04 | (2006.01) |
| C08F 255/02 | (2006.01) |
| C08G 69/48 | (2006.01) |
| B01J 20/32 | (2006.01) |
| C08G 69/10 | (2006.01) |
| C08G 73/02 | (2006.01) |

(52) U.S. Cl.
CPC ............ *B01D 71/78* (2013.01); *B01D 71/56* (2013.01); *B01D 71/76* (2013.01); *B01J 20/321* (2013.01); *B01J 20/3282* (2013.01); *B01J 20/3293* (2013.01); *B01J 20/3297* (2013.01); *C08F 255/02* (2013.01); *C08G 69/48* (2013.01); *C09D 177/04* (2013.01); *C09D 179/02* (2013.01); *G01N 33/54393* (2013.01); *B01D 71/40* (2013.01); *B01D 2323/30* (2013.01); *B01D 2323/385* (2013.01); *C08G 69/10* (2013.01); *C08G 73/022* (2013.01); *C08G 73/0206* (2013.01); *C08G 73/028* (2013.01)

(58) Field of Classification Search
None
See application file for complete search history.

(56) References Cited

U.S. PATENT DOCUMENTS

| 3,018,262 A | 1/1962 | Schroeder |
| 3,298,998 A | 1/1967 | Mcconnell |
| 3,876,738 A | 4/1975 | Marinaccio |
| 3,928,517 A | 12/1975 | Knight |
| 4,157,418 A | 6/1979 | Heilmann |
| 4,539,256 A | 9/1985 | Shipman |
| 4,707,265 A | 11/1987 | Barnes, Jr. |
| 4,726,989 A | 2/1988 | Mrozinski |
| 4,867,881 A | 9/1989 | Kinzer |
| 5,039,549 A | 8/1991 | Nguyen |
| 5,120,594 A | 6/1992 | Mrozinski |
| 5,260,360 A | 11/1993 | Mrozinski |
| 5,458,782 A | 10/1995 | Hou |
| 5,962,544 A | 10/1999 | Waller, Jr. |
| 6,056,529 A | 5/2000 | Meyering |
| 6,267,916 B1 | 7/2001 | Meyering |
| 6,413,070 B1 | 7/2002 | Meyering |
| 6,776,940 B2 | 8/2004 | Meyering |
| 7,125,603 B2 | 10/2006 | David |
| 7,338,692 B2 | 3/2008 | Smith |
| 7,556,858 B2 | 7/2009 | Rasmussen |
| 2005/0142563 A1 | 6/2005 | Haddad |
| 2010/0155323 A1 | 6/2010 | Weiss |
| 2012/0252091 A1 | 10/2012 | Rasmussen |
| 2015/0203645 A1* | 7/2015 | Rasmussen ............ C08J 7/047 524/549 |

FOREIGN PATENT DOCUMENTS

| EP | 0490854 | 6/1992 |
| WO | WO 97-02313 | 1/1997 |
| WO | WO 2009-148869 | 12/2009 |
| WO | WO 2011-109151 | 9/2011 |
| WO | WO 2012-134636 | 10/2012 |

OTHER PUBLICATIONS

Oster, "Ultraviolet Induced Crosslinking and Grafting of Solid High Polymers", Journal of Polymer Science, 1959, vol. 34, pp. 671-684.
Ranby, "Modification of Polymer Surfaces by Photoinduced Graft Copolymerization", Chemical Reactions on Polymers, 168-186 (2009).
Rasmussen, "Polyazlactones", Encyclopedia of Polymer Science and Engineering, 558-571 (1988).

(Continued)

*Primary Examiner* — Krishnan S Menon
(74) *Attorney, Agent, or Firm* — Kent S. Kokko

(57) ABSTRACT

Guanidinyl ligand-functionalized polymers, methods of making the same, and substrates bearing a grafted coating of the ligand-functional polymers are described. The grafted polymer has the requisite affinity for binding neutral or negatively charged biomaterials, such as cells, cell debris, bacteria, spores, viruses, nucleic acids, endotoxins and proteins, at pH's near or below the pI's of the biomaterials.

23 Claims, No Drawings

(56) References Cited

OTHER PUBLICATIONS

Rohr, "Surface Functionalization of Thermoplastic Polymers for the Fabrication of Microfluidic Devices by Photoinitiated Grafting", Advanced Functional Materials, Apr. 2003, vol. 13, No. 4, pp. 264-270.
Tasdelen, "Poly (propylene imine) dendrimers as hydrogen donor in Type II photoinitiated free radical polymerization", European Polymer Journal, 2007, vol. 43, pp. 4423-4430.
Wente, "Manufacture of Superfine Organic Fibers", Naval Research Laboratories Report No. 4364, May 25, 1954, 23 pages.
Wente, "Superfine Thermoplastic Fibers", Industrial and Engineering Chemistry, Aug. 1956, vol. 48, No. 8, pp. 1342-1346.
International Search Report for PCT International Application No. PCT/US2013/042330, mailed on Aug. 16, 2013, 4 pages.

* cited by examiner

GRAFT COPOLYMER FUNCTIONALIZED ARTICLE

CROSS REFERENCE TO RELATED APPLICATIONS

This application is a national stage filing under 35 U.S.C. 371 of PCT/US2013/042330, filed May 23, 2013, which claims priority to Provisional Application No. 61/655,516, filed Jun. 5, 2012, the disclosure of which is incorporated by reference in its/their entirety herein.

TECHNICAL FIELD

The present disclosure relates to ligand-functionalized substrates, and methods for preparing the same. The functionalized substrates are useful in selectively binding and removing biological materials, such as nucleic acids, host cell proteins, endotoxins, and viruses, from biological samples.

BACKGROUND

Detection, quantification, isolation and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules, such as antibodies and enzymes, are important for therapeutic uses and in biomedical research.

In their native state in vivo, structures and corresponding biological activities of these biomacromolecules are maintained generally within fairly narrow ranges of pH and ionic strength. Consequently, any separation and purification operation must take such factors into account in order for the resultant, processed biomacromolecule to have potency.

The use of certain ionic polymers, especially cationic polymers, for the flocculation of cell and/or cell debris, as well as for the precipitation of proteins, is known. Similarly, ionic polymers have been used to modify filtration media to enhance the removal of impurities from process streams in depth filtration or membrane adsorber type applications. The effectiveness of these polymers is typically reduced as the conductivity of the media being processed increases, i.e. as the salt content increases. There is a need in the art for polymeric materials with increased affinity for biological species under high ionic strength conditions.

Chromatographic separation and purification operations can be performed on biological product mixtures, based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of a mobile phase compared to solutes which interact less strongly and, in this fashion, separation and purification can be effected.

Most current capture or purification chromatography is done via conventional column techniques. These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the adsorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Polymeric resins are widely used for the separation and purification of various target compounds. For example, polymeric resins can be used to purify or separate a target compound based on the presence of an ionic group, based on the size of the target compound, based on a hydrophobic interaction, based on an affinity interaction, or based on the formation of a covalent bond. There is a need in the art for polymeric substrates having enhanced affinity for biological materials that allows for selective removal from a biological sample. There is further need in the art for ligand functionalized membranes that overcome limitations in diffusion and binding, and that may be operated at high throughput and at lower pressure drops.

SUMMARY OF THE INVENTION

The present disclosure is directed to ligand-functionalized polymers, methods of making the same, and substrates bearing grafted ligand-functional polymers. More specifically, the substrate comprises grafted thereto a ligand-functionalized polymer and optionally a crosslinked polymer primer layer. The ligand group of the ligand-functional polymer comprises guanidinyl monomers, including guanidine and biguanide containing ligands. The grafted polymer has the requisite affinity for binding neutral or negatively charged biomaterials, such as cells, cell debris, bacteria, spores, viruses, nucleic acids, endotoxins and proteins, at pH's near or below the pI's of the biomaterials.

"Alkyl" means a linear or branched, cyclic or acyclic, saturated monovalent hydrocarbon having from one to about twelve carbon atoms, e.g., methyl, ethyl, 1-propyl, 2-propyl, pentyl, and the like.

"Alkylene" means a linear saturated divalent hydrocarbon having from one to about twelve carbon atoms or a branched saturated divalent hydrocarbon having from three to about twelve carbon atoms, e.g., methylene, ethylene, propylene, 2-methylpropylene, pentylene, hexylene, and the like.

"Alkenyl" means a linear unsaturated monovalent hydrocarbon having from two to about twelve carbon atoms or a branched unsaturated hydrocarbon having from three to about twelve carbon atoms.

"Aryl" means a monovalent aromatic, such as phenyl, naphthyl and the like.

"Arylene" means a polyvalent, aromatic, such as phenylene, naphthalene, and the like.

"Aralkylene" means a group defined above with an aryl group attached to the alkylene, e.g., benzyl, 1-naphthylethyl, and the like.

"Heteroarylene" refers to a divalent group that is aromatic and heterocyclic. That is, the heteroarylene includes at least one heteroatom in an aromatic ring having 5 or 6 members. Suitable heteroatoms are typically oxy, thio, or amino. The group can have one to five rings that are connected, fused, or a combination thereof. At least one ring is heteroaromatic and any other ring can be aromatic, non-aromatic, heterocyclic, carbocyclic, or a combination thereof. In some embodiments, the heteroarylene has up to 5 rings, up to 4 rings, up to 3 rings, up to 2 rings, or one ring. Examples of heteroarylene groups include, but are not limited to, triazine-diyl, pyridine-diyl, pyrimidine-diyl, pyridazine-diyl, and the like.

The term "grafted" is used throughout to indicate that a covalent chemical bond is formed between the substrate and the ligand-functional polymer.

"hydrocarbyl" is inclusive of aryl and alkyl;

"(Hetero)hydrocarbyl" is inclusive of hydrocarbyl alkyl and aryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

"(Hetero)arylene" is inclusive of arylene and heteroarylene.

DETAILED DESCRIPTION

In the article and methods of this invention, ligand-functionalized substrates are provided which have enhanced affinity and/or capacity, especially in high ionic strength media, for biological materials, such as host cell proteins, endotoxins, DNA, RNA, viruses, and other microorganisms, at pH's near or below the pI's of the biological materials. The affinity for such biomaterials allows materials that are positively charged at those pH's, such as antibodies, to be purified, as they are not bound to the ligand functional groups. The ligand functionalized substrate allows the selective capture or binding of target biomaterials by the ligand groups.

In a method of this disclosure, a ligand functionalized substrate is provided by a) providing a substrate, and b) free-radically grafting the substrate in the presence of a Type II photoinitiator with a guanidinyl functional ligand (meth)acryloyl monomer.

In some embodiments the substrate may further comprise a primer layer disposed on the surface thereof, the primer layer comprising the reaction product of: 1) a polyamine polymer, 2) a polyfunctional crosslinking agent for the polyamine polymer, and optionally 3) an amine reactive monomer having a polymerizable, ethylenically unsaturated group, preferably a (meth)acryloyl group, and an amine-reactive functional group. The guanidinyl functional ligand (meth)acryloyl monomer is grafted to the primer layer in the presence of a Type II photoinitiator.

The polymer grafted to the surface of the substrate (or primer layer) comprises polymerized ligand-functional monomer units of the formula 1a or b:

$$\overset{R^1}{\underset{}{=}}\overset{O}{\underset{\|}{C}}-X^1-R^2-\overset{R^3}{\underset{|}{N}}-\left[\overset{NR^3}{\underset{\|}{C}}-\overset{R^3}{\underset{|}{N}}\right]_n-R^4, \text{ or} \quad 1a$$

$$\overset{R^1}{\underset{}{=}}\left[\overset{O}{\underset{\|}{C}}-X^1-R^2\right]_o\overset{R^5}{\underset{\|}{=}}N-N-\left[\overset{NR^3}{\underset{\|}{C}}-\overset{R^3}{\underset{|}{N}}\right]_n-R^4 \quad 1b$$

wherein
$R^1$ is H or $C_1$-$C_4$ alkyl;
$R^2$ is a (hetero)hydrocarbyl group, preferably a divalent alkylene having 1 to 20 carbon atoms;
each $R^3$ is independently H or hydrocarbyl, preferably $C_1$-$C_{12}$ alkyl;
$R^4$ is H, $C_1$-$C_{12}$ alkyl or —$N(R^3)_2$;
$R^5$ is H or hydrocarbyl, preferably $C_1$-$C_{12}$ alkyl or aryl;
$X^1$ is —O— or —$NR^3$—,
o is 0 or 1, and
n is 1 or 2.

The grafted polymer comprises 10 to 100 parts by weight of the guanidinyl monomer units, i.e. the grafted (co)polymer may comprise a homopolymer of guanidinyl monomer units.

Such ligand monomers may be made by condensation of an alkenyl or alkenoyl compound, typically a (meth)acryloyl halide, a (meth)acryloylisocyanate, or an alkenylazlactone, with a compound of formulas 2a or 2b:

$$HX^1-R^2-\overset{R^3}{\underset{|}{N}}-\left[\overset{NR^3}{\underset{\|}{C}}-\overset{R^3}{\underset{|}{N}}\right]_n-R^4, \text{ or} \quad 2a$$

$$H_2N-\overset{R^3}{\underset{|}{N}}-\left[\overset{NR^3}{\underset{\|}{C}}-\overset{R^3}{\underset{|}{N}}\right]_n-R^4 \quad 2b$$

where $X^1$, $R^2$ to $R^4$, and n are as previously defined.

Other ligand monomers may be made by condensation of a carbonyl containing monomer, such as acrolein, vinylmethylketone, diacetone acrylamide or acetoacetoxyethylmethacrylate, optionally in the presence of a reducing agent, with a compound of formulas 2a or 2b.

Optionally, the ligand-functional alkenyl (co)polymer layer also comprises units derived from a (meth)acryloyl monomer containing at least two free radically polymerizable groups. Such multifunctional (meth)acryloyl monomers, including (meth)acrylate and (meth)acrylamide monomers may be incorporated into the blend of polymerizable monomers to assist in branching or lightly crosslinking of the grafted ligand-functional copolymer. Examples of useful multifunctional (meth)acrylates include, but are not limited to, di(meth)acrylates, tri(meth)acrylates, and tetra(meth)acrylates, such as ethyleneglycol di(meth)acrylate, 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, methylenebisacrylamide, ethylenebisacrylamide, hexamethylenebisacrylamide, diacryloylpiperazine, and mixtures thereof.

Surprisingly, it has been found that, in some embodiments, inclusion of such a multifunctional (meth)acrylate or (meth)acrylamide monomer increases the capacity, particularly the dynamic binding capacity, of the grafted article for capturing biological species. Such comonomers are used in amounts of about 0.25 to about 5 parts by weight, preferably of about 1 to about 3 parts by weight, relative to 100 parts total monomer weight. Higher concentrations of polyfunctional comonomer often lead to decreased capacities. While not wanting to be bound by theory, it is believed that this comonomer promotes branching in the grafted (co)polymer layer, thereby leading to increased accessibility or availability of the ligand groups.

The ligand-functional alkenyl (co)polymer layer (optionally grafted to the primer layer) may optionally comprise one or more hydrophilic monomers which comprise at least one alkenyl group, preferably a (meth)acryloyl group, and a hydrophilic group, including poly(oxyalkylene) and ionic groups, for providing hydrophilicity to the substrate, or for providing greater selectivity to the substrate when binding biomaterials.

The hydrophilic ionic groups may be neutral, have a positive charge, a negative charge, or a combination thereof. With some suitable ionic monomers, the ionic group can be neutral or charged depending on the pH conditions. This class of monomers is typically used to impart a desired hydrophilicity to the porous base substrate. In certain applications, the addition of a grafting ionic monomer having a positive charge at the selected pH may be used to increase the charge density of the grafted copolymer, allowing increased selectivity of binding or increased capacity of binding for negatively charged contaminants while repelling positively charged biological materials.

In some preferred embodiments, the third monomer may have an acrylate group, or other ethylenically unsaturated groups of reduced reactivity, and a poly(alkylene oxide) group; e.g. monoacrylated poly(alkylene oxide) compounds, where the terminus is a hydroxy group or an alkyl ether group.

In some embodiments the ionic monomers having a negative charge include (meth)acryloylsulfonic acids of Formula 3 or salts thereof.

3 wherein, Y is a straight or branched alkylene (e.g., an alkylenes having 1 to 10 carbon atoms, 1 to 6 carbon atoms, or 1 to 4 carbon atoms) and L is —O— or —NR$^3$—, where R$^3$ is H or C$_1$-C$_{12}$ alkyl; R$^1$ is H or C$_1$-C$_4$ alkyl; and Y is an alkylene (e.g., an alkylene having 1 to 10 carbon atoms, 1 to 6, or 1 to 4 carbon atoms). Exemplary ionic monomers according to Formula 3 include, but are not limited to, N-acrylamidomethanesulfonic acid, 2-acrylamidoethanesulfonic acid, 2-acrylamido-2-methyl-1-propanesulfonic acid, and 2-methacrylamido-2-methyl-1-propanesulfonic acid. Salts of these acidic monomers can also be used. Counter ions for the salts can be, for example, ammonium ions, potassium ions, lithium ions, or sodium ions.

Other suitable ionic grafting monomers having a negative charge (at a selected pH) include sulfonic acids such as vinylsulfonic acid and 4-styrenesulfonic acid; phosphonic acids such as vinylphosphonic acid, (meth)acrylamidoalkylphosphonic acids (e.g., 2-(meth)acrylamidoethylphosphonic acid and 3-(meth)acrylamidopropylphosphonic acid; acrylic acid and methacrylic acid; and carboxyalkyl(meth)acrylates such as 2-carboxyethyl(meth)acrylate, and 3-carboxypropyl(meth)acrylate. Still other suitable acidic monomers include (meth)acryloylamino acids, such as those described in U.S. Pat. No. 4,157,418 (Heilmann). Exemplary (meth)acryloylamino acids include, but are not limited to, N-acryloylglycine, N-acryloylaspartic acid, N-acryloyl-β-alanine, and 2-acrylamidoglycolic acid. Salts of any of these acidic monomers can also be used.

Some exemplary ionic grafting monomers that are capable of providing a positive charge (at a selected pH) are amino (meth)acrylates or amino (meth)acrylamides of Formula 4 or quaternary ammonium salts thereof. The counterions of the quaternary ammonium salts are often halides, sulfates, phosphates, nitrates, and the like.

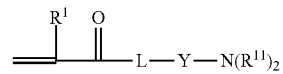

4 where L is —O— or —NR$^3$—, where R$^1$ is H or C$_1$-C$_{12}$ alkyl-; and Y is an alkylene (e.g., an alkylene having 1 to 10 carbon atoms, 1 to 6, or 1 to 4 carbon atoms). Each R$^{11}$ is independently hydrogen, alkyl, hydroxyalkyl (i.e., an alkyl substituted with a hydroxy), or aminoalkyl (i.e., an alkyl substituted with an amino). Alternatively, the two R$^{11}$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

In some embodiments of Formula 4, both R$^{11}$ groups are hydrogen. In other embodiments, one R$^{11}$ group is hydrogen and the other is an alkyl having 1 to 10, 1 to 6, or 1 to 4 carbon atoms. In still other embodiments, at least one of R$^{11}$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the R$^{11}$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexene, or cyclohexane. Exemplary heterocyclic groups fused to an additional ring include, but are not limited to, benzoimidazolyl.

Exemplary amino acrylates (i.e., L in Formula 4 is —O—) include N,N-dialkylaminoalkyl acrylates such as, for example, N,N-dimethylaminoethylacrylate, N,N-dimethylaminoethylmethacrylate, N,N-diethylaminoethyl acylate, N,N-diethylaminoethylmethacrylate, N,N-dimethylaminopropylacrylate, N,N-dimethylaminopropylmethacrylate, N-tert-butylaminopropylmethacrylate, N-tert-butylaminopropylacrylate and the like.

Exemplary amino (meth)acrylamides, (i.e., L in Formula 4 is —NR$^3$—) include, for example, N-(3-aminopropyl)methacrylamide, N-(3-aminopropyl)acrylamide, N-[3-(dimethylamino)propyl]methacrylamide, N-(3-imidazolylpropyl)methacrylamide, N-(3-imidazolylpropyl)acrylamide, N-(2-imidazolylethyl)methacrylamide, N-(1,1-dimethyl-3-imidazoylpropyl)methacrylamide, N-(1,1-dimethyl-3-imidazoylpropyl)acrylamide, N-(3-benzoimidazolylpropyl)acrylamide, and N-(3-benzoimidazolylpropyl)methacrylamide.

Exemplary quaternary salts of the ionic monomers of Formula 4 include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Neutral hydrophilic monomers that may be incorporated are poly(alkylene oxide) monomers having a (meth)acryloyl or non-acryloyl ethylenically unsaturated group and a non-polymerizable terminus. Such monomers may be of the formula 5:

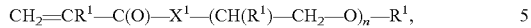

wherein each $R^1$ is independently H or $C_1$-$C_4$ alkyl, $X^1$ is —O— or —$NR^3$—, where $R^3$ is H or $C_1$-$C_{12}$ alkyl and n is 2 to 100.

Others include the alkenylazlactones adducts of polyetheramines (such as the monoamine, diamine and triamines based on the polyetheramine structure). One example of these compounds is the Jeffamine® series, from Huntsman, The Woodlands, Tex., USA. Other useful neutral, hydrophilic comonomers include dimethylacrylamide, acrylamide, methacrylamide, hydroxyethyl(meth)acrylate, hydroxypropyl(meth)acrylate, N-vinylpyrrolidinone, or combinations thereof.

Such optional hydrophilic comonomers are used in amounts of about 0 to 90 parts by weight, 1 to about 90 parts by weight, preferably of about 5 to about 50 parts by weight, relative to 100 parts total monomer weight. However, when the hydrophilic monomer is an anionic monomer, it is used in amounts of 15 parts be weight or less, so as to not reduce the ability of the grafted substrate to interact with and capture negatively charged biological materials.

As result of the method described herein, the substrate is provided with a grafted polymer of the formula 10:

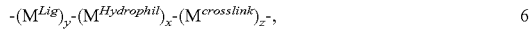

where
$(M^{Lig})_y$ are guanidinyl ligand functional monomer units having "y" polymerized monomer units,
$(M^{Hydrophil})_x$ are hydrophilic monomer units having "x" polymerized monomer units,
$(M^{crosslink})$ are multifunctional (meth)acrylate monomer units having "z" polymerized monomer units,
y is 10 to 100 parts by weight of the $(M^{Lig})$ monomer units;
x is 0 to 90 parts by weight of the $(M^{hydrophil})$ monomer units;
z is 0 to 5 parts by weight of the $(M^{Crosslink})$ monomer units, where the total is 100 parts by weight.

It will be understood the monomer units are simplified for clarity and monomers other than the depicted $M^{lig}$ monomer may be covalently bonded with the substrate. It is believed that the multifunctional acrylate will crosslink the grafted ligand functional polymer, and/or will further provide grafted hyperbranched polymers with ligand functional groups. It is further believed that minor amounts of free, ungrafted polymer may be present on the surface of the substrate, which may further be crosslinked and/or hyperbranched to the extent that it is physically entangled with the grafted copolymer.

The substrate may be in any form such as particles, fibers, films or sheets. Suitable particles include, but are not limited to, organic particles, inorganic particles, and porous and nonporous particles. Preferably the base substrate is porous. Suitable porous base substrates include, but are not limited to, porous particles, porous membranes, porous nonwoven webs, and porous fibers The substrate may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

In some embodiments, the thermoplastic polymer may be surface treated, such as by plasma discharge, to provide suitable functionality to the surface of the substrate. Surface treatment provides functional groups such as hydroxyl groups that can improve wetting by the coating or optional primer solution. One such useful plasma treatment is described in U.S. Pat. No. 7,125,603 (David et al.).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly (iminoadipolyliminohexamethylene), poly(iminoadipolyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

A preferred substrate is a porous substrate that is a microporous membrane such as a solvent-induced phase separation (SIPS) membrane. In this embodiment the porous base substrate comprises a nylon microporous film or sheet, such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. No. 3,928,517, U.S. Pat. No. 4,707,265 (Knight et al.), and U.S. Pat. No. 5,458,782 (Hou et al.).

In another embodiment, the porous substrate is a thermally-induced phase separation (TIPS) membrane. These are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Microporous membranes are further disclosed in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

The substrate may be in any form such as films or sheets. Preferably the base substrate is porous. Suitable porous base substrates include, but are not limited to, porous membranes, porous woven and nonwoven webs, and porous fibers.

In many embodiments, the base substrate has an average pore size that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of biological materials. The efficiency of binding other target molecules may confer different optimal ranges.

In other embodiments, the porous base substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by wet laid, carded, air laid, spunlaced, spunbonding or meltblowing techniques or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly dispersed meltblown fibers. Any of the non-woven webs may be made from a single type of fiber or two or more fibers that differ in the type of thermoplastic polymer and/or thickness.

Further details on the manufacturing method of nonwoven webs of this invention may be found in Wente, Superfine Thermoplastic Fibers, 48 INDUS. ENG. CHEM. 1342(1956), or in Wente et al., Manufacture Of Superfine Organic Fibers, (Naval Research Laboratories Report No. 4364, 1954).

The substrate optionally has a primer layer disposed on the substrate comprising the reaction product of: 1) a polyamine polymer, 2) a polyfunctional crosslinking agent for the polyamine polymer, and 3) an amine reactive monomer having a polymerizable, ethylenically unsaturated group, preferably a (meth)acryloyl group, and an amine-reactive functional group; and c) a ligand-functional alkenyl (co)polymer layer grafted to the primer layer. The primer layer is coated on the substrate and cured to form a durable, crosslinked polyamine polymer layer having polymerizable, ethylenically unsaturated groups, preferably (meth)acryloyl groups, on the surface thereof. The crosslinking of the polyamine polymer is effected by the 2) polyfunctional crosslinking agent, which has two or more amine-reactive functional groups, such as epoxy groups. The crosslinked polyamine polymer is simultaneously or sequentially functionalized with primer component 3), having an amine-reactive group for coupling (by forming a covalent bond) to the crosslinked polyamine polymer, and an ethylenically unsaturated group, such as a (meth)acryloyl group, which may be used to free-radically graft the c) ligand-functional alkenyl (co)polymer layer to the crosslinked polyamine polymer layer.

The primer base polymer comprises a polyamine polymer; i.e. a polymer having primary or secondary amino groups that may be pendant or catenary, i.e. in the polymer chain. The aminopolymers contain primary or secondary amine groups and can be prepared by chain growth or step growth polymerization procedures with the corresponding monomers. These monomers can also, if desired, be copolymerized with other monomers. The polymer can also be a synthesized or naturally occurring biopolymer. If any of these polymers, irrespective of source, do not contain primary or secondary amine groups, these functional groups can be added by the appropriate chemistry.

Useful aminopolymers are water soluble or water-dispersible. As used herein, the term "water soluble" refers to a material that can be dissolved in water. The solubility is typically at least about 1 milligram, preferably 5 milligram, more preferably 10 milligram, per milliliter of water. As used herein, the term "water dispersible" refers to a material that is not water soluble but that can be emulsified or suspended in water. In some embodiments mixed aqueous/alcoholic solvent systems may be advantageous.

Examples of aminopolymers suitable for use, which are prepared by chain growth polymerization include, but are not limited to: polyvinylamine, poly(N-methylvinylamine), polyethylenimine, polypropylenimine, polyallylamine, polyallylmethylamine, polydiallylamine, poly(4-aminomethylstyrene), poly(4-aminostyrene), poly(acrylamide-co-methylaminopropylacrylamide), and poly(acrylamide-co-aminoethylmethacrylate).

Examples of amino polymers suitable for use, which are prepared by step growth polymerization include, but are not limited to: polyethylenimine, polypropylenimine, polylysine, polyornithine, polyaminoamides, polydimethylamine-epichlorohydrin-ethylenediamine, and certain polyaminosiloxanes, which can be built from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Useful aminopolymers may also include those that have primary or secondary amino end groups and include, but are not limited to, those formed from polyamidoamine (PAMAM) and polypropylenimine: e.g. DAB-Am and PAMAM dendrimers (or hyperbranched polymers containing the amine functional group). Dendrimeric material formed from PAMAM are commercially available under the trade designation Starburst™ (PAMAM) dendrimer (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical, Milwaukee, Wis. Dendrimeric material formed from polypropylenimine is commercially available under the trade designation "DAB-AM" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of aminopolymers suitable for use, which are biopolymers include chitosan, glucosamine- and galactosamine-containing polysaccharides, and starch, where the latter is reacted with reagents such as methylaminoethylchloride.

Other categories of aminopolymers suitable for use include polyacrylamide homo- or copolymers with amino monomers including aminoalkyl(meth)acrylate, (meth)acrylamidoalkylamine, and diallylamine.

Preferred aminopolymers include polyamidoamines, polyethyleneimine, polyvinylamine, polyallylamine, and polydiallylamine.

Suitable commercially available aminopolymers include, but are not limited to, polyamidoamines such as ANQUAMINE™ 360, 401, 419, 456, and 701 (Air Products and Chemicals, Allentown, Pa.); LUPASOL™ polyethylenimine polymers such as FG, PR 8515, Waterfree, P, PS (BASF Corporation, Rensselaer, N.Y.); polyethylenimine polymers such as CORCAT™ P-600 (EIT Company, Lake Wylie, S.C.); and polyamide resins such as the VERSAMID series of resins that are formed by reacting a dimerized unsaturated fatty acid with polyalkylene polyamines (Cognis Corporation, Cincinnati, Ohio).

The primer layer has a crosslinking agent for the polyamine polymer having at least two amine-reactive functional groups, including ketone, aldehyde, ester, acyl halide, isocyanate, epoxide, anhydride, or azlactone groups. Preferably the amine-reactive functional groups Z are selected to react with the amine groups of the polyamine polymer at temperatures below about 50° C., preferably below 25° C. such that the crosslinking reaction takes place during the coating and drying operation. Preferable crosslinking agents are further water-soluble or water-dispersible.

Such crosslinking agents may have the general formula 1:

$$R^8-(Z)_y, \qquad 7$$

where $R^8$ is a (hetero)hydrocarbyl group, Z is an amine-reactive group and y is $\geq 2$, preferably 2-4. The $R^8$ group may be an alkylene group, an arylene group, a heteroarylene group, a heteroalkylene group, an aralkylene group, or a combination thereof.

In one embodiment the amine-reactive Z group may be an epoxy group and include both aliphatic and aromatic polyepoxides. Representative examples of aliphatic polyepoxides include 3',4'-epoxycyclohexylmethyl-3,4-epoxycyclohexanecarboxylate, 3,4-epoxycyclohexyloxirane, 2-(3',4'-epoxycyclohexyl)-5,1"-spiro-3",4"-epoxycyclohexane-1,3-dioxane, bis(3,4-epoxycyclohexylmethyl)adipate, the diglycidyl ester of linoleic dimer acid, 1,4-bis(2,3-epoxypropoxy)butane, 4-(1,2-epoxyethyl)-1,2-epoxycyclohexane, 2,2-bis(3,4-epoxycyclohexyl)propane, polyglycidyl ethers of aliphatic polyols such as glycerol, ethylene glycol, polyethylene glycol or butanediol. Representative examples of aromatic polyepoxides which can be utilized in the composition of the invention include glycidyl esters of aromatic carboxylic acids, e.g., phthalic acid diglycidyl ester, isophthalic acid diglycidyl ester, trimellitic acid triglycidyl ester, and pyromellitic acid tetraglycidyl ester, and mixtures thereof; N-glycidylaminobenzenes, e.g., N,N-diglycidylbenzeneamine, bis(N,N-diglycidyl-4-aminophenyl)methane, 1,3-bis(N,N-diglycidylamino)benzene, and N,N-diglycidyl-4-glycidyloxybenzeneamine, and mixtures thereof; and the polyglycidyl derivatives of polyhydric phenols, e.g., 2,2-bis-[4-(2,3-epoxypropoxy)phenyl]propane, the polyglycidyl ethers of polyhydric phenols such as tetrakis (4-hydroxyphenyl)ethane, pyrocatechol, resorcinol, hydroquinone, 4,4'-dihydroxydiphenyl methane, 4,4'dihydroxydiphenyl dimethyl methane, 4,4'-dihydroxy-3,3'-dimethyldiphenyl methane, 4,4'-dihydroxydiphenyl methyl methane, 4,4'-dihydroxydiphenyl cyclohexane, 4,4'-dihydroxy-3,3'-dimethyldiphenyl propane, 4,4'-dihydroxydiphenyl sulfone, and tris-(4-hydroxyphenyl)methane, polyglycidyl ethers of novolacs (reaction products of monohydric or polyhydric phenols with aldehydes in the presence of acid catalysts), and the derivatives described in U.S. Pat. Nos. 3,018,262 and 3,298,998, the descriptions of which are incorporated herein by reference, as well as the derivatives described in the Handbook of Epoxy Resins by Lee and Neville, McGraw-Hill Book Co., New York (1967), and mixtures thereof.

In one embodiment the amine reactive functional group Z may be an isocyanate group. Suitable polyisocyanates include organic compounds containing at least two free isocyanate groups. Diisocyanates of the formula $R^8(NCO)_2$ are preferably used wherein $R^8$ denotes an aliphatic hydrocarbon group with 4 to 20 carbon atoms, a cycloaliphatic hydrocarbon group with 6 to 20 carbon atoms, an aromatic hydrocarbon group with 6 to 20 carbon atoms or an araliphatic hydrocarbon group with 7 to 20 carbon atoms.

Examples of diisocyanates include tetramethylene diisocyanate, hexamethylenediisocyanate (HDI), dodecamethylenediisocyanate, 1,4-diisocyanatocyclohexane, 1-isocyanato-3,3,5-trimethyl-5-isocyanatomethylcyclohexane (IPDI), 4,4'-diisocyanato-dicyclohexylmethane (HMDI), 4,4'-diisocyanato-2,2-dicyclohexyl-propane, 1,4-diisocyanatobenzene, 2,4-diisocyanatotoluene (TDI), 2,6-diisocyanatotoluene, 4,4'-diisocyanatodiphenylmethane (MDI), m- and p-xylylenediisocyanate, $\alpha,\alpha,\alpha',\alpha'$-tetramethyl-m- and p-xylylenediisocyanate and mixtures of these compounds. Suitable polyisocyanates also include triisocyanates such as 1,3,5-triisocyanatocyclohexane.

In one embodiment the amine reactive functional group Z may be an azlactone group. Reference may be made to Table 1 of a review entitled "Polyazlactones" by J. K. Rasmussen, et al., Encyclopedia of Polymer Science and Engineering, Second Edition, Volume 11, 1988, pp. 558-571 that contains a listing of reported bis(azlactones). Other poly azlactone functional materials are described in U.S. Pat. No. 7,556,858 (Rasmussen et al.), incorporated herein by reference.

In one embodiment the amine reactive functional group Z may be an aldehyde or ketone group. Examples include bis- and polyaldehydes, such as glyoxal or glutaraldehyde.

In some embodiments the crosslinking agent may be a polyacyl compound where Z is an ester, acid, acid halide or anhydride group. Esters and acids are less preferred due to the reduced reactivity. Representative examples of suitable diacyl compounds, as the corresponding esters, halides, acids, and anhydrides: azelaic; maleic; fumaric; itaconic; 1,5-pent-2-enedioic; adipic; 2-methyleneadipic; 3-methylitaconic; 3,3-dimethylitaconic; sebacic; suberic; pimelic; succinic; benzylsuccinic; sulfosuccinic; glutaric; 2-methyleneglutaric; 2-sulfoglutaric; 3-sulfoglutaric; diglycolic; dilactic; 3,3'-(ethylenedioxy)dipropionic; dodecanedioic; 2-sulfododecanedioic; decanedioic; undecanedicarboxylic; hexadecanedicarboxylic; dimerized fatty acids (such as those obtained by the dimerization of olefinically unsaturated monocarboxylic acids containing 16 to 20 carbon atoms, for example, oleic acid and linoleic acid and the like); 1,2-, 1,4-, and 1,6-cyclohexanedicarboxylic; norbornenedicarboxylic; bi-cyclooctanedicarboxylic; and other aliphatic, heteroaliphatic, saturated alicyclic, or saturated heteroalicyclic dicarboxylic acids; and the like; and mixtures thereof. Salts (for example, alkali metal salts) of the above-described sulfonic acids can also be used.

The crosslinking agent for the polyamine polymer may be provided in an amount wherein the number of equivalents of amine reactive groups Z is at least 2%, preferably at least 5%, and up to about 20%, relative to the number of equivalents of amine groups in the polyamine polymer.

The primer layer optionally further comprises an amine reactive monomer having a polymerizable, ethylenically unsaturated group and an amine-reactive functional group, some embodiments of which are of the formula 8:

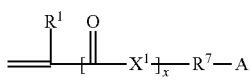   8 wherein
$X^1$ is —O— or —NR$^3$—, where R$^3$ is H or $C_1$-$C_{12}$ alkyl,
$R^1$ is H or $C_1$-$C_4$ alkyl;
$R^7$ is a single bond or a (hetero)hydrocarbyl linking group,
A is a functional group that is reactive with the amino groups of the polyamine polymer, and
x is 0 or 1.

In some embodiments compounds of Formula 8 are (meth)acryloyl compounds, and in other embodiments are alkenyl compounds.

Preferably, $R^7$ is a single bond or a hydrocarbyl linking group that joins an ethylenically unsaturated, polymerizable group (e.g. alkenyl or (meth)acryl group) to reactive functional group A and preferably is an alkylene group having 1 to 6 carbon atoms, a 5- or 6-membered cycloalkylene group having 5 to 10 carbon atoms, or a divalent aromatic group having 6 to 16 carbon atoms; and A is a reactive functional group capable of reacting with an amine group of the polyamine polymer for the incorporation of a free-radically polymerizable group.

Useful reactive functional groups "A" include carboxyl, oxazolinyl, azlactone, acetyl, acetonyl, acetoacetyl, ester, isocyanato, epoxy, aziridinyl, acyl halide, and cyclic anhydride groups. Preferably the amine-reactive functional groups A are selected to react with the amine groups of the polyamine polymer at temperatures below about 50° C., preferably below 25° C. such that the reaction takes place during the coating and drying operation. Preferable amine reactive monomers are further water-soluble or water-dispersible.

Representative azlactone group-substituted functional compounds of Formula 2 include: 2-ethenyl-1,3-oxazolin-5-one; 2-ethenyl-4-methyl-1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-3-oxa-1-aza[4.5]spirodec-1-ene-4-one; 2-ethenyl-5,6-dihydro-4H-1,3-oxazin-6-one; 2-ethenyl-4,5,6,7-tetrahydro-1,3-oxazepin-7-one; 2-isopropenyl-5,6-dihydro-5,5-di(2-methylphenyl)-4H-1,3-oxazin-6-one; 2-acryloyloxy-1,3-oxazolin-5-one; 2-(2-acryloyloxyl)ethyl-4,4-dimethyl-1,3-oxazolin-5-one; 2-ethenyl-4,5-dihydro-6H-1,3-oxazin-6-one; and 2-ethenyl-4,5-dihydro-4,4-dimethyl-6H-1,3-oxazin-6-one.

Representative acetoacetyl group-substituted functional compounds of Formula 8 include 2-(acetoacetoxy)ethyl methacrylate.

Representative carboxyl group-substituted functional compounds of Formula 8 include (meth)acrylic acid, 3-(meth)acryloyloxy-propionic acid, 4-(meth)acryloyloxy-butyric acid, 2-(meth)acryloyloxy-benzoic acid, 3-(meth)acryloyloxy-5-methyl benzoic acid, 4-(meth)acryloyloxymethyl-benzoic acid, phthalic acid mono-[2-(meth)acryloyloxy-ethyl]ester, 2-butynoic acid, and 4-pentynoic acid.

Representative isocyanate group-substituted functional compounds of Formula 8 include 2-isocyanatoethyl (meth)acrylate, 3-isocyanatopropyl (meth)acrylate, 4-isocyanatocyclohexyl (meth)acrylate, 4-isocyanatostyrene, 2-methyl-2-propenoyl isocyanate, 4-(2-(meth)acryloyloxyethoxycarbonylamino) phenylisocyanate, allyl 2-isocyanatoethylether, and 3-isocyanato-1-propene.

Representative epoxy group-substituted functional compounds of Formula 8 include glycidyl (meth)acrylate, thioglycidyl (meth)acrylate, 3-(2,3-epoxypropoxy)phenyl (meth)acrylate, 2-[4-(2,3-epoxypropoxyl)phenyl]-2-(4-(meth)acryloyloxy-phenyl)propane, 4-(2,3-epoxypropoxyl) cyclohexyl (meth)acrylate, 2,3-epoxycyclohexyl (meth)acrylate, and 3,4-epoxycyclohexyl (meth)acrylate.

Representative acyl halide group-substituted functional compounds of Formula 8 include (meth)acryloyl chloride, α-chloro(meth)acryloyl chloride, (meth)acryloyloxyacetyl chloride, 5-hexenoyl chloride, 2-(acryloyloxy) propionyl chloride, 3-(acryloylthioxy) propionoyl chloride, and 3-(N-acryloyl-N-methylamino) propionoyl chloride.

Other useful amine-reactive monomers include anhydride group-substituted functional monomers including maleic anhydride, (meth)acrylic anhydride, itaconic anhydride, 3-(meth)acryloyloxyphthalic anhydride, and 2-(meth)acryloxycyclohexanedicarboxylic acid anhydride.

In the method of the invention, the ligand-functionalized monomer is graft (co)polymerized onto the substrate, which may be primed or unprimed. Typically, the substrate is coated with an imbibing solution comprising the ligand-functionalized monomer, any comonomers, a Type II photoinitiator, and a solvent for the mixture.

The Type II photoinitiator is used in an amount effective to facilitate hydrogen abstraction from the surface of the substrate to provide an incipient free radical, and free radical addition of the monomer(s) to produce the grafted (co)polymer. The photoinitiators can be used in amounts from about 0.001 part by weight to about 15 parts, preferably from about 0.5 to about 5 parts, by weight based on 100 parts total monomer.

The method further comprises a radiation-sensitive hydrogen abstracting photoinitiator having the general formula:

   9 in which Ar is a substituted or unsubstituted aryl group having 6 to 12 carbon atoms optionally substituted with a $C_1$ to $C_{12}$ alkyl group, a $C_1$ to $C_{12}$ alkoxy group, or a phenyl group; and $R^{13}$ is a $C_1$ to $C_6$ alkyl group, a cycloalkyl group having 3 to 14 carbon atoms, or Ar Included among those hydrogen abstracting photoinitiators encompassed by Formula 9 include benzophenone, 4-(3-sulfopropyloxyl)benzophenone sodium salt, Michler's ketone, benzil, anthraquinone, 5,12-naphthacenequinone, aceanthracenequinone, benz(A)anthracene-7,12-dione, 1,4-chrysenequinone, 6,13-pentacenequinone, 5,7,12,14-pentacenetetrone, 9-fluorenone, anthrone, xanthone, thioxanthone, 2-(3-sulfopropyloxyl)thioxanthen-9-one, acridone, dibenzosuberone, acetophenone, and chromone.

The above-described ligand functionalized substrates may be prepared using a combination of process steps. The method comprises:

1) providing a base substrate, preferably a porous base substrate;
2) imbibing the substrate (preferably imbibing the porous substrate) with a solution or suspension comprising (a) one or more guanidinyl ligand functional monomers of Formulas Ia and/or Ib (b) optionally one or more hydrophilic monomers; c) optionally one or more multifunctional monomers; and d) a Type II photoinitiator.
3) exposing the coated substrate (or imbibed porous base substrate) to UV radiation so as to form free radicals on the surface(s) of the base substrate by hydrogen abstraction, and graft-polymerizing the ethylenically unsaturated, free-radically polymerizable groups of the monomers onto the surface of the base substrate.

The solvent for the imbibing solution may be any polar solvent. In many embodiments the solvent is water or a water/water-miscible organic solvent mixture. The ratio of water to organic solvent can vary widely, depending upon monomer solubility. With some monomers, it is typically greater than 1:1 (v/v) water to organic solvent, preferably greater than 5:1, and more preferably greater than 7:1. With other monomers, a higher proportion of organic solvent, even up to 100%, with some alcohols especially, may be preferred.

Any such water miscible organic solvent preferably has no groups that would retard the polymerization. In some embodiments, the water miscible solvents are protic group containing organic liquids such as the lower alcohols having 1 to 4 carbon atoms, lower glycols having 2 to 6 carbon atoms, and lower glycol ethers having 3 to 6 carbon atoms and 1 to 2 ether linkages. In some embodiments higher glycols such as poly(ethylene glycol) may be used. Specific examples are methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and mixtures thereof.

In other embodiments, non-protic water miscible organic solvents that can also be used such as aliphatic esters and ketones and sulfoxides methoxyethyl acetate, ethoxyethyl acetate, propoxyethyl acetate, butoxyethyl acetate, triethyl phosphate, acetone, methyl ethyl ketone, methyl propyl ketone and dimethyl sulfoxide.

The concentration of each component in the imbibing solution may vary depending on a number of factors including, but not limited to, the grafting monomer or monomers in the imbibing solution, the extent of grafting desired, the reactivity of the grafting monomer(s), and the solvent used. Typically, the total concentration of the monomers in the imbibing solution ranges from about 0.1 wt % to about 60 wt %, desirably, from about 1 wt % to about 35 wt %, more desirably, from about 5% to about 25%, based on a total weight of the imbibing solution. Following grafting, washing, and drying, typical total weight gains by the substrate are in the range of about 5% to about 30%, in the range of about 10% to about 25%, or in the range of about 12% to about 20%.

UV light sources can be relatively low light intensity sources such as blacklights which provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers, or relatively high light intensity sources such as medium pressure mercury lamps which provide intensities generally greater than 10 mW/cm$^2$, preferably between 15 and 450 mW/cm$^2$.

Where UV radiation is used to fully or partially polymerize the composition, moderate intensities and longer exposure times are preferred. For example, an intensity of about 10 to 50 mW/cm$^2$ and an exposure time of about 1 to 5 seconds may be used successfully. Alternatively, an exposure time of up to about 30 minutes may be used. A preferred UV source is the Quant 48™ UV Curing System from Quantum Technologies, Irvine, Calif.

Subsequent to the grafting steps the grafted substrate may be subjected to an optional washing/rinsing step, where the functionalized substrate is washed or rinsed one or more times in a rinse chamber to remove any unreacted monomers, solvent or other reaction by-products from the functionalized substrate. Typically, the functionalized substrate is washed or rinsed up to four times using a water rinse, a saline rinse, and optionally an alcohol rinse, a combination of water and alcohol rinses, and/or a solvent rinse (e.g., acetone, MEK, etc). When an alcohol rinse is used, the rinse may include one or more alcohols including, but not limited to, isopropanol, methanol, ethanol, or any other alcohol that is practical to use and an effective solvent for any residual monomer. In each rinse step, the functionalized substrate may pass through a rinse bath or a rinse spray.

In the optional drying step, the functionalized substrate is dried to remove any rinse solvent from the functionalized substrate. Typically, the functionalized substrate is dried in an oven having a relatively low oven temperature for a desired period of time (referred to herein as "oven dwell time"). Oven temperatures typically range from about 30° C. to about 120° C., while oven dwell times typically range from about 120 to about 600 seconds. Any conventional oven may be used in the optional drying step. Suitable ovens include, but are not limited to, convection ovens and recirculating air ovens.

In the above-described methods of making a functionalized substrate, any of the above-mentioned porous base substrates, grafting monomers, and reactants may be used to form a given functionalized substrate. The porous base substrate is often in the form of a porous membrane such as a microporous membrane, a nonwoven web, or porous fibers. In some embodiments, the porous base substrate comprises a microporous membrane formed by a solvent-induced phase separation (SIPS) method.

In one embodiment, the methods provide an article having a ligand functionalized coating covalently grafted on the surface thereof, the ligand functionalized coating comprising the UV polymerization reaction product of a one or more ligand monomers, one or more ethylenically unsaturated crosslinking monomers and one or more hydrophilic monomers, the free radical polymerization product being the result of hydrogen abstraction from the surface of the substrate.

The method of making a ligand functionalized substrate alters the original nature of the porous base substrate, as the grafted and UV polymerized species include a ligand group. The method enables the formation of ligand functionalized substrates having many of the advantages of a porous bases substrate (e.g., mechanical and thermal stability, porosity), but with enhanced affinity for biomolecules such as nucleic acids, host cell proteins, endotoxins, and microbes, resulting from the monomers and steps used to form a given functionalized substrate.

The porous substrates having a coating of ligand-functionalized polymer are particularly suited as filter media, for the selective binding and removal of target biological species including proteins, cells, cell debris, microbes, nucleic acids, and/or viruses from biological samples. The present disclosure further provides a method for the removal of target biological species from a biological sample by contacting the sample with the ligand polymer functionalized substrate as described herein. As used herein "target biological species" may include a contaminant or a species of interest.

The ligand functionalized substrate is useful for the purification of biological or other fluid samples comprising biologically derived species (biological species). Biological species include, but are not limited to, cells, cell debris, proteins, nucleic acids, endotoxins, and viruses.

In some embodiments, the biological species being removed from the fluid is the object of the purification. For example, a recombinant protein or enzyme may be prepared in cell culture or by fermentation, and the substrate can be used to capture the protein or enzyme as the first step in the purification process. In another example, the substrate may be used to capture microorganisms from a fluid as the first step in a process of concentrating, enumerating, and/or identifying the microorganisms.

In other embodiments, the biological species being removed from the fluid is a contaminant that must be removed prior to additional processing steps for the fluid.

Significantly, many of the ligand functional substrates are useful under conditions of high salt concentration or high ionic strength, i.e., they are "salt tolerant". The term "salt" is meant to include all low molecular weight ionic species which contribute to the conductivity of the solution. The importance of utility of the ligand functional substrates in the presence of salt is that many process solutions used in biopharmaceutical or enzyme manufacture have conductivities in the range of 15-30 mS/cm (approximately 150-300 mM salt) or more. Salt tolerance can be measured in comparison to that of the conventional quaternary amine or Q ligand (e.g. trimethylammonium ligand), whose primarily electrostatic interactions with many biological species rapidly deteriorates at conductivities three- to six-fold less than the target range of 15-30 mS/cm. For example, when attempting to remove positively charged proteins such as host cell proteins through the use of filtration devices functionalized with conventional Q ligands, the process fluid may have to be diluted two-fold or more in order to reduce the conductivity to an acceptable range. This is expensive and dramatically increases the overall processing time. Surprisingly, it has been found that ligand functionalized substrates in which the ligands comprise guanidine or biguanide groups perform extremely well under high ionic strength conditions.

The biological sample is contacted with the ligand functionalized substrate for a time sufficient to interact and form a complex with the target biological species disposed (dissolved or suspended) in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 50% of its original concentration. It is more preferred that the solution is contacted with the ligand functionalized substrate for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 10% of its original concentration. It is still more preferred that the solution is contacted with the ligand functionalized substrate for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 1% of its original concentration.

In many embodiments the substrate may be functionalized so that other proteins are excluded or repelled from the ligand functionalized substrate, while negatively charged biological species bind to the ligand functional groups of Formulas Ia and Ib. Surprisingly, it has been found that negatively charged biological species bind tenaciously to the ligand functional group of Formulas Ia and Ib. This finding is particularly advantageous when the target biological species is a contaminant and the ligand functionalized substrate is part of a disposable filtration or purification device. However, when the target biological species is the object of isolation or purification, it is important to be able to elute the captured species from the functionalized substrate. In such instances, the strength of the interaction with the ligand functionalized substrate may be reduced by lowering the amount of monomer of Formula 1a or 1b in the grafted copolymer. In these cases, as previously described, the substrate may be grafted with one or more ionic comonomers. In particular, the porous substrate may comprise grafted ionic groups that are positively charged at the selected pH of the biological sample solution to increase the charge density of the grafted copolymer, allowing increased selectivity of binding or increased capacity of binding for negatively charged species, yet by virtue of not being salt-tolerant, will allow elution of the target species by a change in pH or salt concentration.

The substrate for capture of target biological species may be any previously described, but is preferably a microporous membrane. The membrane pore size desired is from 0.1 to 10 µm, preferably 0.5 to 3 micrometers and most preferably 0.8 to 2 micrometers. A membrane with a high surface area for the internal pore structure is desired, which typically corresponds to fine pore sizes. However, if the pore size is too small, then the membrane tends to plug with fine particulates present in the sample solution.

If desired, efficiency of binding and capture may be improved by using a plurality of stacked, ligand-functionalized porous membranes as a filter element. Thus the present disclosure provides a filter element comprising one or more layers of the porous, ligand functionalized substrate. The individual layers may be the same or different, and may have layers of different porosity, and degree of grafting by the aforementioned grafting monomers. The filter element may further comprise an upstream prefilter layer and downstream support layer. The individual filter elements may be planar or pleated as desired.

Examples of suitable prefilter and support layer materials include any suitable porous membranes of polypropylene, polyester, polyamide, resin-bonded or binder-free fibers (e.g., glass fibers), and other synthetics (woven and nonwoven fleece structures); sintered materials such as polyolefins, metals, and ceramics; yarns; special filter papers (e.g., mixtures of fibers, cellulose, polyolefins, and binders); polymer membranes; and others.

In another embodiment, there is provided a filter cartridge including the above-described filter element. In yet another embodiment there is provided a filter assembly comprising the filter elements and a filter housing. In a further embodiment, this invention relates to a method of biological species capture comprising the steps of:

a) providing the filter element comprising one of more layers of the ligand functionalized base substrate of this disclosure, and b) allowing a moving biological solution containing a target biological species to impinge upon the upstream surface of the filter element for a time sufficient to effect binding of the target species.

The present disclosure is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

As used herein, all ratios and percentages are by weight unless otherwise indicated. Reagents and solvents were obtained from Sigma Aldrich; St. Louis Mo., unless indicated otherwise.

Test Methods
Static BSA Capacity Method for Functionalized Substrates

Functionalized substrates were analyzed for static binding capacity by rocking one disk of the substrate in a solution of the test analyte overnight. The disk was prepared by die-punching a 24-mm diameter disk from a sheet of the substrate. Each disk was placed in a 5 mL centrifuge tube with 4.5 mL of BSA (bovine serum albumin) challenge solution (Catalog # A-7906) at a concentration of about 3.0 mg/ml in 25 millimolar TRIS (tris(hydroxymethyl)aminomethane) buffer, pH 8.0. The tubes were capped, and tumbled on a rotating mixer overnight (typically 14 hours) on a rotating mixer. The supernatant solutions were analyzed using a UV-VIS spectrometer at 279 nm (with background correction applied at 325 nm). The static binding capacity for each substrate was determined by comparison to the absorption of the starting BSA solution, and results are reported in mg/mL as the average of three replicates.

Dynamic BSA Capacity Method for Functionalized Substrates

Functionalized substrates were analyzed for dynamic binding of proteins by a passing solution of the test analyte through a 6-layer stack of the substrate. The stack was prepared by die-punching 25-mm diameter disks from a sheet of the substrate and placing the stack in a 25 mm diameter holder attached to an AKTA chromatography system (GE Healthcare, NY). BSA was prepared at a concentration 1 mg/mL in 25 millimolar TRIS buffer containing 50 millimolar NaCl, pH 8.0. The BSA challenge solution was pumped through the substrate stack at a flow rate of 1 mL/min and the UV absorbance of the effluent was monitored at a wavelength of 280 nm. The dynamic binding capacity of the substrate was evaluated using standard chromatography techniques, and reported in mg/mL at 10% breakthrough.

Static Lysozyme Capacity Method for Functionalized Substrates

Functionalized substrates were analyzed as described for the Static BSA capacity method with a challenge solution of lysozyme instead of BSA. Lysozyme (Catalog # L6876- 10G) was prepared at a concentration of about 3.0 mg/mL in 10 millimolar MOPS (3-(N-morpholino) propanesulfonic acid,) buffer, pH 7.5.

Static IgG Capacity Method for Functionalized Substrates

Functionalized substrates were analyzed as described for the Static BSA capacity method with for a challenge solution of human immunoglobulin (IgG) instead of BSA. Human IgG (Catalog # SLH66, Equitech-Bio, Kerrville Tex.) was prepared at a concentration of about 1.5 mg/mL in 50 millimolar sodium acetate with 40 millimolar NaCl buffer, pH 4.5.

Preparation of Primed Nylon Membrane Substrate (S1)

Polyethylenimine (PEI—MW 70,000, a 30% by weight aqueous solution, Cat#00618; Polysciences, Inc.; Warrington Pa.) was diluted to 1.0% solids with IPA (isopropanol). A 50 gram portion of this solution was formulated with enough butanediol diglycidyl ether (BUDGE, 106 microliter, Sigma Aldrich) to react with 5 mole % of the amine groups of the polymer. Primed substrates were prepared by dipping a 10 square centimeter piece of a nylon 66 membrane (single reinforced layer nylon three zone membrane, nominal pore size 1.8 µm, #080ZN from 3M Purification, Inc.; Meridan Conn.), into the coating solution, removing excess coating solution with a #14 wire-wound coating rod, then allowing the substrate to air dry at ambient temperature for at least 15 minutes.

Preparation of Primed Nylon Membrane Substrate 2 (S2)

A priming solution and primed substrate were prepared as described for membrane substrate 1 except that enough glycidylmethacrylate was added to the polyethylenimine/butanediol diglycidyl ether priming solution to react with 10 mole % of the amine groups of the PEI polymer.

Unprimed Nylon Membrane Substrate 3 (S3)

Unprimed membrane substrate S3 was a nylon 66 membrane (single reinforced layer nylon three zone membrane, nominal pore size 1.8 µm, #080ZN from 3M Purification, Inc.; Meridan Conn.

Preparation of Unprimed Nylon Nonwoven Substrate 4 (S4)

Substrate S4 was prepared according the procedure for the Preparation of Nylon Nonwoven Substrate A in U.S. Patent Publication No. 20100155323. The substrate was prepared to a basis weight of 60 grams per square meter (gsm) using 4.3 EFD Nylon B24 Nylon 6 polymer; BASF).

Preparation of Unprimed Polypropylene Nonwoven Substrate (S5)

Substrate S5 is a 50 gsm polypropylene SMS nonwoven web (4148 Kiara™ Filtration Media—20% 4-point square bond; PGI Polymers Inc., Mooresville N.C.). SMS indicates a layered construction having a layer of melt blown fibers laminated between two spun-bonded fiber layers.

Preparation of Polyethylene TIPS Membrane Substrate (S6)

Membrane substrate S6 is a 4.5 mil thick polyethylene TIPS (thermally induced phase separation) membrane having a 1.30 micrometer pore size and 85% porosity that was prepared as described in U.S. Pat. No. 4,539,256.

Preparation of Polypropylene TIPS Membrane Substrate (S7)

Membrane S7 is a 4.5 mil thick polypropylene TIPS membrane having a 0.80 micrometer pore size and 85% porosity that was prepared as described in U.S. Pat. Nos. 4,726,989, and 5,120,594.

Examples 1-6

IEM-AGM sodium sulfate (4-(2-(methacryloyloxy)-ethylaminocarbonylamino)butylguanidinium sodium sulfate) was prepared according Example 99 of PCT Patent Publication Number US2012/024310, filed February 2012, which was based on U.S. Patent Application No. 61/468,302 filed Mar. 28, 2011.

Coating solutions (5 grams each) were prepared in methanol from IEM-AGM sodium sulfate, MBA, and benzophenone in the amounts listed in Table 2. To aid in formulation, a 50 mg/mL solution of MBA in methanol and a 0.5 g/mL solution of benzophenone in methanol were first prepared. Portions of these solutions were micropipetted to each coating solution to obtain the desired amount of monomer and photoinitiator in the coating solution. In Table 2, the amounts of IEM-AGM and benzophenone are listed as w/w % in the total solution, while MBA is listed as w/w % based on the amount of IEM-AGM. Primed substrates 51 were coated, grafted, and washed as described in Example 1. BSA binding capacities are shown in Table 1.

TABLE 1

| Example | IEM-AGM (w/w %) | MBA % | benzophenone (w/w %) | BSA Capacity (mg/mL) Static | BSA Capacity (mg/mL) Dynamic |
|---|---|---|---|---|---|
| 4 | 14 | 0 | 0.1 | 57 | Not determined |
| 5 | 14 | 1 | 0.1 | 101 | 78 |
| 6 | 14 | 2 | 0.1 | 116 | 89 |
| 7 | 14 | 3 | 0.1 | 133 | 81 |
| 8 | 16 | 2 | 0.1 | 118 | 88 |
| 9 | 18 | 2 | 0.5 | 103 | 87 |

Examples 7-13

Coating solutions were prepared in methanol from IEM-AGM, MBA, and benzophenone as described above in Example 1. Example 13 also included 4.2% w/w PEG200 methacrylate as a co-monomer. Unprimed substrates S3 were coated, grafted, and washed as described in Example 1. BSA binding capacities are shown in Table 2.

TABLE 2

| Example | IEM-AGM (w/w %) | MBA % | Benzophenone (w/w %) | BSA Capacity (mg/mL) Static | BSA Capacity (mg/mL) Dynamic |
|---|---|---|---|---|---|
| 7 | 14 | 2 | 2 | 138 | 102 |
| 8 | 14 | 2 | 1 | 136 | 74 |
| 9 | 14 | 2 | 0.5 | 135 | 100 |
| 10 | 14 | 2 | 0.1 | 142 | 71 |
| 11 | 12 | 2 | 0.5 | 111 | 79 |
| 12 | 10 | 2 | 0.5 | 102 | 64 |
| 13 | 14 | 2 | 0.5 | 112 | 102 |

Examples 14-17

Coating solutions were prepared as described in Example 1, except the coating solvent was DI (deionized) water, and the benzophenone was replaced by S-BP (a water soluble benzophenone, 4-(3-sulfopropyloxyl)benzophenone, sodium salt prepared as described in Japanese patent 47040913). Substrates S3 were coated, grafted, and washed as described in Example 1. BSA binding capacities are shown in Table 3.

TABLE 3

| Example | IEM-AGM (w/w %) | MBA % | S-BP (w/w %) | BSA Capacity (mg/mL) Static | BSA Capacity (mg/mL) Dynamic |
|---|---|---|---|---|---|
| 14 | 14 | 2 | 2 | 39 | 27 |
| 15 | 14 | 2 | 1 | 51 | 30 |
| 16 | 14 | 2 | 0.5 | 69 | 40 |
| 17 | 14 | 2 | 0.1 | 73 | 37 |

Examples 18-25

Coating solutions were prepared as described in Example 13, except that portions of the IEM-AGM were replaced by dimethylacrylamide (DMA) or 2-hydroxyethylmethacrylate (HEMA). Substrates S3 were coated, grafted, washed and dried as described in Example 1. BSA binding capacities are shown in Table 4.

TABLE 4

| Example | IEM-AGM (w/w %) | DMA (w/w %) | HEMA (w/w %) | BSA Capacity (mg/mL) Static | BSA Capacity (mg/mL) Dynamic |
|---|---|---|---|---|---|
| 18 | 12 | 2 | — | 137 | 85 |
| 19 | 10 | 4 | — | 141 | 72 |
| 20 | 8 | 6 | — | 132 | 58 |
| 21 | 6 | 8 | — | 101 | 39 |
| 22 | 12 | — | 2 | 135 | 87 |
| 23 | 10 | — | 4 | 131 | 78 |
| 24 | 8 | — | 6 | 132 | 61 |
| 25 | 6 | — | 8 | 103 | 41 |

Examples 26-27

Coating solutions were mixed having the compositions shown in Table 5. Each of the solutions included 2% w/w MBA based on total monomer weight and 0.5% w/w photoinitiator based on the total solution weight. Substrates were coated grafted washed and dried as in Example 1 except that Examples 48 and 49 were coated onto substrate S6, and Example 50 was coated onto substrate S7. BSA binding capacities are shown in Table 5.

TABLE 5

| Ex | IEM-AGM (w/w %) | Solvent | Photoinitiator | Static BSA Capacity (mg/mL) |
|---|---|---|---|---|
| 26 | 14 | Methanol | BP | 109 |
| 27 | 14 | Methanol | BP | 93 |

Examples 28-35

Coating solutions containing IEM-AGM (14% w/w) and PEG400 methacrylate (5.6% w/w) in methanol were prepared. The amounts of MBA (wt % based on IEM-AGM) and benzophenone (BP) varied as shown in Table 10. Substrates S2 were coated, grafted, washed and dried as described in Example 1. BSA binding capacities are listed in Table 6.

TABLE 6

| Example | MBA (%) | BP (w/w %) | BSA Capacity (mg/mL) Static | BSA Capacity (mg/mL) Dynamic |
|---|---|---|---|---|
| 28 | 3 | 0.125 | 144 | 82 |
| 29 | 3 | 0.500 | 135 | 83 |
| 30 | 2 | 0.250 | 143 | 89 |
| 31 | 1 | 0.125 | 137 | 95 |
| 32 | 1 | 0.500 | 137 | 92 |
| 33 | 0 | 0.125 | 125 | 93 |
| 34 | 0 | 0.250 | 129 | 117 |
| 35 | 0 | 0.500 | 125 | 113 |

Examples 36-40

Coating solutions were prepared in 1:1 w/w methanol/DI water from VDM-AGM, sodium sulfate salt ($N^2$-acryloyl-$N^1$-(4-{[amino(imino)methyl]amino}butyl)-2-methylalaninamide) at the % solids shown in Table 7. The VDM-AGM was prepared as described in Applicant's copending U.S. Ser. No. 13/353,413, example 52. Each solution also contained 2% MBA based on the amount of VDM-AGM and 0.5% BP. Substrates S3 were coated and sandwiched between polyester sheets as described in Example 1. UV grafting was conducted using a UV stand (Classic Manufacturing, Inc., Oakdale, Minn.) equipped with 18 bulbs (Sylvania RG2 40W F40/350BL/ECO, 10 above and 8 below the substrate, 46 inches long, spaced 2 inches on center), with an irradiation time of 7 minutes. After grafting, the samples were washed, dried, and evaluated for BSA binding capacities. Results are shown in Table 7.

TABLE 7

| Example | VDM-AGM (w/w %) | BSA Capacity (mg/mL) Static | BSA Capacity (mg/mL) Dynamic |
|---|---|---|---|
| 36 | 8 | 67 | 44 |
| 37 | 10 | 91 | 56 |
| 38 | 12 | 116 | 78 |
| 39 | 14 | 131 | 89 |
| 40 | 16 | 145 | 91 |

This disclosure provides the following embodiments:
1. A method of preparing a ligand functional substrate comprising the steps of:
   a) providing a substrate,
   b) free-radically grafting the substrate in the presence of a Type II photoinitiator with a guanidinyl-functional (meth)acryloyl monomer of the formula:

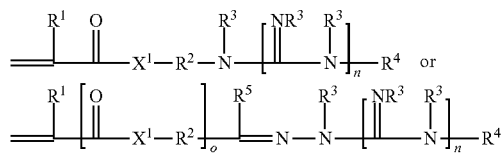

wherein
$R^1$ is H or $C_1$-$C_4$ alkyl;
$R^2$ is a (hetero)hydrocarbyl group;
each $R^3$ is independently H or hydrocarbyl;
$R^4$ is H, $C_1$-$C_{12}$ alkyl or —$N(R^3)_2$;
$R^5$ is H or hydrocarbyl;
$X^1$ is —O— or —$NR^3$—;
o is 0 or 1, and
n is 1 or 2.

2. The method of embodiment 1 wherein the substrate is provided with a primer layer disposed on the substrate comprising the reaction product of:
   1) a polyamine polymer; and
   2) a polyfunctional crosslinking agent for the polyamine polymer.
3. The method of embodiment 1 wherein the substrate is provided with a primer layer disposed on the substrate comprising the reaction product of:
   1) a polyamine polymer;
   2) a polyfunctional crosslinking agent for the polyamine polymer; and
   3) an amine-reactive monomer having an amine-reactive functional group and an ethylenically unsaturated, polymerizable group, to provide a substrate having a crosslinked polyamine primer layer on the substrate, the primer layer having pendent alkenyl groups.
4. The method of any of the previous embodiments further comprising grafting the substrate with a hydrophilic monomer.
5. The method of any of the previous embodiments further comprising grafting with a multifunctional (meth)acryloyl monomer.
6. The method of any of the previous embodiments wherein the Type II photoinitiator is a benzophenone photoinitiator.
7. The method of embodiment 6 wherein the benzophenone photoinitiator is water-soluble.
8. The method of any of the previous embodiments comprising the step of imbibing the substrate with a monomer mixture comprising:
   a) up to 100 parts by weight of guanidinyl monomers,
   b) 0 to 90 parts by weight of hydrophilic monomer units, and
   c) 0 to about 5 by weight parts by weight of multifunctional (meth)acryloyl monomer wherein the total monomer is 100 parts by weight.
9. The method of embodiment 8 wherein the imbibing monomer mixture comprises about 0.1 wt % to about 60 wt % of monomers in an organic or aqueous solvent.
10. The method of any of the previous embodiments wherein the grafted monomers form a grafted copolymer of the formula:

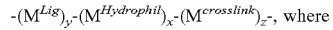

$(M^{Hydrophil})_x$ are hydrophilic monomer units having "x" polymerized monomer units, $(M^{Lig})_y$ are ligand functional monomer units having "y" polymerized monomer units, $(M^{crosslink})$ are multifunctional (meth)acrylate monomer units having "z" polymerized monomer units.
11. The method of embodiment 4 wherein the hydrophilic monomer units comprise poly(oxyalkylene) (meth)acrylate monomer units.
12. The ligand-functional substrate of embodiment 11, wherein the poly(oxyalkylene) (meth)acrylate monomer units are of the formula: $CH_2$=$CR^1$—$C(O)$—$X^1$—$(CH(R^1)$—$CH_2$—$O)_n$—$R^1$, wherein each $R^1$ is independently H or $C_1$-$C_4$ alkyl, $X^1$ is —O— or —$NR^3$—, where $R^3$ is H or $C_1$-$C_4$ alkyl and n is 2 to 100.
13. The method of embodiment 1 wherein the substrate comprises a primer layer disposed on the substrate comprising a crosslinked polyamine polymer having ethylenically unsaturated polymerizable groups.
14. The method of embodiment 13 wherein the crosslinked polyamine polymer having ethylenically unsaturated polymerizable groups is the reaction product of:
   1) a polyamine polymer;
   2) a polyfunctional crosslinking agent for the polyamine polymer; and 3) a monomer having an amine-reactive functional group and an ethylenically unsaturated polymerizable group.

15. The method of any of the previous embodiments wherein the polyamine polymer is selected from the group consisting of polyethylenimine, polylysine, polyaminoamides, poly-dimethylamine-epichlorohydrin-ethylenediamine, polyaminosiloxanes and dendrimers formed from polyamidoamine (PAMAM) and polypropylenimine.

16. The method of any of the previous embodiments wherein said primer layer comprises 0.1 to 5 wt. % of the substrate.

17. The method of embodiment 10 wherein said (co)polymer comprises 5 to 30 wt. % of the ligand functional substrate.

18. A method of separating a target biological species from a fluid comprising contacting the fluid with the ligand-functionalized substrate prepared by the method of any of the previous embodiments whereby a complex comprising the functionalized substrate and the target biological species is formed, and separating the complex; wherein said target biological species is selected from biomacromolecules and microbiological species.

19. The method of embodiment 18 wherein said biomacromolecules are selected from proteins, enzymes, nucleic acids, and endotoxins.

20. The method of embodiment 18 wherein said microbiological species is selected from bacteria, viruses, cells, cell debris, and spores.

21. The method of embodiment 20 wherein the cells are selected from archaea, bacteria, and eucaryota.

22. The method of embodiments 18 to 21 wherein the biological fluid is derived from a cell culture or fermentation process.

23. The method of embodiments 18 to 21 wherein the biological fluid comprises a solution of a purified protein or enzyme after separating the target species.

24. The method of embodiment 23 wherein the separated target species comprises a purified protein or enzyme.

25. The method of embodiments 18 to 21 wherein the fluid has a salt content of at least 50 millimolar.

26. An article comprising:
   a) a substrate, and
   b) grafted to the surface of the substrate (co)polymer comprising interpolymerized of guanidinyl-functional (meth)acryloyl monomer units of the formula:

$$\underset{}{\overset{R^1}{=}}\overset{O}{\underset{}{\|}}-X^1-R^2-N\underset{}{\overset{R^3}{\|}}\overset{NR^3}{\underset{}{\|}}-N\underset{n}{\overset{R^3}{\|}}R^4 \quad \text{or}$$

$$\underset{}{\overset{R^1}{=}}\left[\overset{O}{\underset{}{\|}}-X^1-R^2\right]_o\overset{R^5}{\underset{}{\|}}-N-N\underset{}{\overset{R^3}{\|}}\overset{NR^3}{\underset{}{\|}}-N\underset{n}{\overset{R^3}{\|}}R^4$$

wherein
$R^1$ is H or $C_1$-$C_4$ alkyl;
$R^2$ is a (hetero)hydrocarbyl group;
each $R^3$ is independently H or hydrocarbyl;
$R^4$ is H, $C_1$-$C_{12}$ alkyl or $-N(R^3)_2$;
$R^5$ is H or hydrocarbyl;
$X^1$ is $-O-$ or $-NR^3-$;
o is 0 or 1, and
n is 1 or 2.

27. The article of embodiment 26 wherein the grafted copolymer further comprises hydrophilic monomer units.

28. The article of embodiment 26 wherein the grafted polymer comprises:
   a) up to 100 parts by weight of guanidinyl monomers,
   b) 0 to 90 parts by weight of hydrophilic monomer units, and
   c) 0 parts by weight of multifunctional (meth)acryloyl monomer
   wherein the total monomer is 100 parts by weight.

29. The article of embodiment 26 wherein the grafted copolymer is of the formula:

-$(M^{Lig})_y$-$(M^{hydrophil})_x$-, where $(M^{hydrophil})_x$ are hydrophilic monomer units having "x" polymerized monomer units, and
$(M^{Lig})_y$ are guanidinyl functional ligand monomer units having "y" polymerized monomer units.

30. The article of any of embodiments 26-29 wherein the hydrophilic monomer units comprise poly(oxyalkylene) (meth)acrylate monomer units.

31. The ligand-functional substrate of embodiment 30, wherein the poly(oxyalkylene) (meth)acrylate monomer units are of the formula: $CH_2=CR^1-C(O)-X^1-(CH(R^1)-CH_2-O)_n-R^1$, wherein each $R^1$ is independently H or $C_1$-$C_4$ alkyl, $X^1$ is $-O-$ or $-NR^3-$, where $R^3$ is H or $C_1$-$C_4$ alkyl and n is 2 to 100.

32. The ligand-functional substrate of any of embodiments 26-31 wherein the grafted (co)polymer is uncrosslinked.

What is claimed is:

1. A method of preparing a ligand functional substrate comprising the steps of:
   a) providing a substrate,
   b) free-radically grafting the substrate in the presence of a Type II photoinitiator of the general formula:

$Ar-CO-R^{13}$ in which Ar is a substituted or unsubstituted aryl group having 6 to 12 carbon atoms optionally substituted with a $C_1$ to $C_{12}$ alkyl group, a $C_1$ to $C_{12}$ alkoxy group, or a phenyl group; and
$R^{13}$ is a $C_1$ to $C_6$ alkyl group, a cycloalkyl group having 3 to 14 carbon atoms, or Ar;
   with a guanidinyl-functional (meth)acryloyl monomer of the formula:

$$\underset{}{\overset{R_1}{=}}\overset{O}{\underset{}{\|}}-X^1-R^2-N\underset{}{\overset{R^3}{\|}}\overset{NR^3}{\underset{}{\|}}-N\underset{n}{\overset{R^3}{\|}}R^4 \quad \text{or}$$

$$\underset{}{\overset{R_1}{=}}\left[\overset{O}{\underset{}{\|}}-X^1-R^2\right]_o\overset{R^5}{\underset{}{\|}}-N-N\underset{}{\overset{R^3}{\|}}\overset{NR^3}{\underset{}{\|}}-N\underset{n}{\overset{R^3}{\|}}R^4$$

wherein
$R^1$ is H or $C_1$-$C_4$ alkyl;
$R^2$ is a (hetero)hydrocarbyl group;
each $R^3$ is independently H or hydrocarbyl;
$R^4$ is H, $C_1$-$C_{12}$ alkyl or $-N(R^3)_2$;
$R^5$ is H or hydrocarbyl;
$X^1$ is $-O-$ or $-NR^3-$;
o is 0 or 1, and
n is 1 or 2; and
wherein the substrate is provided with a primer layer disposed on the substrate comprising the reaction product of:
1) a polyamine polymer; and
2) a polyfunctional crosslinking agent for the polyamine polymer.

2. The method of claim 1 wherein the substrate is provided with a primer layer disposed on the substrate comprising the reaction product of:
1) a polyamine polymer;
2) a polyfunctional crosslinking agent for the polyamine polymer; and 3) an amine-reactive monomer having an amine-reactive functional group and an ethylenically unsaturated, polymerizable group, to provide a substrate having a crosslinked polyamine primer layer on the substrate, the primer layer having pendent alkenyl groups.

3. The method of claim 1 further comprising grafting the substrate with a hydrophilic monomer.

4. The method of claim 1 further comprising grafting with a multifunctional (meth)acryloyl monomer.

5. The method of claim 1 wherein the Type II photoinitiator is a benzophenone photoinitiator.

6. The method of claim 1 comprising the step of free-radically grafting the substrate with a monomer mixture comprising:
   a) up to 100 parts by weight of guanidinyl monomers,
   b) 0 to 90 parts by weight of hydrophilic monomer units, and
   c) 0 to about 5 by weight parts by weight of multifunctional (meth)acryloyl monomer wherein the total monomer is 100 parts by weight.

7. The method of claim 6 wherein the monomer mixture comprises about 0.1 wt % to about 60 wt % of monomers in an organic or aqueous solvent.

8. The method of claim 1 wherein the grafted monomers form a grafted copolymer of the formula:

$-(M^{Lig})_y-(M^{Hydrophil})_x-(M^{crosslink})_z-$, where $(M^{Hydrophil})_x$ are hydrophilic monomer units having "x" polymerized monomer units, $(M^{Lig})_y$ are ligand functional monomer units having "y" polymerized monomer units, $(M^{crosslink})$ are multifunctional (meth)acrylate monomer units having "z" polymerized monomer units.

9. The method of claim 3 wherein the hydrophilic monomer units comprise poly(oxyalkylene) (meth)acrylate monomer units.

10. The method of claim 9, wherein the poly(oxyalkylene) (meth)acrylate monomer units are of the formula: $CH_2=CR^1-C(O)-X^1-(CH(R^1)-CH_2-O)_n-R^1$, wherein each $R^1$ is independently H or $C_1$-$C_4$ alkyl, $X^1$ is —O— or —$NR^3$—, where $R^3$ is H or $C_1$-$C_4$ alkyl and n is 2 to 100.

11. The method of claim 1 wherein the substrate comprises a primer layer disposed on the substrate comprising a crosslinked polyamine polymer having ethylenically unsaturated polymerizable groups.

12. The method of claim 11 wherein the crosslinked polyamine polymer having ethylenically unsaturated polymerizable groups is the reaction product of:
   1) a polyamine polymer;
   2) a polyfunctional crosslinking agent for the polyamine polymer; and
   3) a monomer having an amine-reactive functional group and an ethylenically unsaturated polymerizable group.

13. The method of claim 2 wherein the polyamine polymer is selected from the group consisting of polyethylenimine, polylysine, polyaminoamides, polydimethylamine-epichlorohydrin-ethylenediamine, polyaminosiloxanes and dendrimers formed from polyamidoamine (PAMAM) and polypropylenimine.

14. The method of claim 2 wherein said primer layer comprises 0.1 to 5 wt. % of the substrate.

15. The method of claim 8 wherein said (co)polymer comprises 5 to 30 wt. % of the ligand functional substrate.

16. A method of separating a target biological species from a fluid comprising contacting the fluid with the ligand-functionalized substrate prepared by the method of claim 1 whereby a complex comprising the functionalized substrate and the target biological species is formed, and separating the complex; wherein said target biological species is selected from biomacromolecules and microbiological species.

17. The method of claim 16 wherein said biomacromolecules are selected from proteins, enzymes, nucleic acids, and endotoxins.

18. The method of claim 16 wherein said microbiological species is selected from bacteria, viruses, cells, cell debris, and spores.

19. The method of claim 18 wherein the cells are selected from archaea, bacteria, and eucaryota.

20. The method of claim 16 wherein the biological fluid is derived from a cell culture or fermentation process.

21. The method of claim 16 wherein the biological fluid comprises a solution of a purified protein or enzyme after separating the target species.

22. The method of claim 21 wherein the separated target species comprises a purified protein or enzyme.

23. The method of claim 16 wherein the fluid has a salt content of at least 50 millimolar.

* * * * *

UNITED STATES PATENT AND TRADEMARK OFFICE
CERTIFICATE OF CORRECTION

PATENT NO. : 9,616,394 B2
APPLICATION NO. : 14/400810
DATED : April 11, 2017
INVENTOR(S) : Bothof et al.

It is certified that error appears in the above-identified patent and that said Letters Patent is hereby corrected as shown below:

In the Specification

Column 1,
Line 7, after "U.S.C." insert -- § --.

Column 3,
Line 16, delete "phenoxyethoxyl)" and insert -- phenoxyethoxy) --, therefor.

Column 6,
Line 42, delete "diethylaminoethyl acylate," and insert -- diethylaminoethylacrylate, --, therefor.

Column 7,
Line 37, delete "($M^{crosslink}$)" and insert -- ($M^{crosslink}$)$_z$ --, therefor.
Line 61, after "fibers" insert -- . --.

Column 11,
Line 64, delete "epoxypropoxyl)" and insert -- epoxypropoxy) --, therefor.
Line 67, delete "4,4'dihydroxydi-" and insert -- 4,4'-dihydroxydi- --, therefor.

Column 12,
Line 50, delete "diacyl" and insert -- diacetyl --, therefor.

Column 14,
Line 17, delete "epoxypropoxyl)" and insert -- epoxypropoxy) --, therefor.
Line 18, delete "epoxypropoxyl)" and insert -- epoxypropoxy) --, therefor.
Line 55, after "Ar" insert -- . --.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*

Column 24,
Line 46, delete "$(M^{crosslink})$" and insert -- $(M^{crosslink})_z$ --, therefor.

Column 26,
Line 7, delete "$(M^{hydrophil})_x$-," and insert -- $(M^{Hydrophil})_x$-, --, therefor
Line 8, delete "$(M^{hydrophil})_x$" and insert -- $(M^{Hydrophil})_x$ --, therefor.

In the Claims

Column 27,
Line 31, in Claim 8, delete "$(M^{crosslink})$" and insert -- $(M^{crosslink})_z$ --, therefor.